United States Patent [19]

Binder

[11] Patent Number: 4,787,885

[45] Date of Patent: * Nov. 29, 1988

[54] HYDROGEL SETON

[76] Inventor: Perry S. Binder, 6870 La Valle Plateada, Rancho Santa Fe, Calif. 92062

[*] Notice: The portion of the term of this patent subsequent to Jan. 6, 2004 has been disclaimed.

[21] Appl. No.: 22,558

[22] Filed: Mar. 6, 1987

Related U.S. Application Data

[63] Continuation of Ser. No. 767,190, Aug. 19, 1985, abandoned, which is a continuation-in-part of Ser. No. 597,530, Apr. 6, 1984, Pat. No. 4,634,418.

[51] Int. Cl.$^4$ .................................... A61M 27/00
[52] U.S. Cl. ........................................ 604/8; 604/93; 604/294; 623/4
[58] Field of Search ............... 604/8, 93, 175, 264, 604/294, 9; 623/4, 5, 66

[56] References Cited

U.S. PATENT DOCUMENTS

| | | | |
|---|---|---|---|
| 3,915,172 | 10/1975 | Wichterle et al. | 604/8 |
| 3,948,271 | 4/1976 | Akiyama | 604/49 |
| 3,949,750 | 4/1976 | Freeman | 604/294 |
| 4,021,382 | 5/1977 | Stoy et al. | 3/1 |
| 4,036,230 | 7/1977 | Adams | 604/294 |
| 4,037,604 | 7/1977 | Newkirk | 604/9 |
| 4,428,746 | 1/1984 | Mendez | 604/8 |
| 4,521,210 | 6/1985 | Wong | 604/8 |

OTHER PUBLICATIONS

Surgical Management of Chronic Glaucoma in Aphakia; A. Robert Bellows, MD, Murray A. Johnstone, MD; *Ophthalmology*, vol. 90, No. 7, Jul. 1983.
Long-Term Results of Valve Implants in Filtering Surgery for Eyes with Neovascular Glaucoma; Theodore Krupin, MD, Paul Kaufman, MD, Alan I. Mandell, MD, Stuart A. Terry, MD, Robert Ritch, MD, Steven M. Podos, MD and Bernard Becker, MD; *American Journal of Ophthalmology*, vol. 94, No. 6, Jun. 1983.
The Mai Hydrophilic Implant for Scleral Buckling: a Review, *Ophthalmic Surgery;* Ho, P. C., Chan, I. M., Refojo, M. F. and Tolentino, F. I., vol. 15, pp. 511–515, 1984.
Experimental Seton Procedures in Rabbits; Bloomenthal, M., Harris, L. S., Gaylen, M. A., *Surgical Forum*, vol. 20, 1969, (no pages listed).
Silicon Catheters used as Setons in Glaucoma Surgery; Egerer, I., *Glaucoma*, vol. 5, No. 1, pp. 32–34, 1983.
Draining Implant for Neovascular Glaucoma; Kuljaca, Z., Ljubojevic, V., Momirov, D., *American Journal of Ophthalmology*, vol. 96, pp. 372–276, 1983.
Anterior Chamber Tube Shunt to an Encircling Band in the Treatment of Neovascular Glaucoma, Schocket, S. S., Lakhantal, V., and Richards, R. D., *Ophthalmology*, vol. 89, pp. 1188–1194, 1982.
Gold Leaf Seton for Lowering Intraocular Pressure; Wolkowicz, M. I., Krishna, N. and Hallett, J. W., *Annals of Opthalmology*, vol. 2, pp. 527–541, 1971.
Valve Implants in Filtering Surgery; Krupin T. Podos, S. M., and Becker, B., and Newkirk, J. B., *American Journal of Ophthalmology*, vol. 81, pp. 232–235, 1976.
Preservation of Ultrastructure of Cells Cultured on Protein–Hydroxyethylmethacrylate Hydrogels; Toselli, P., Farris, B., Oliver, P., Wedel, N., and Franzblau, C., *A Journal of Ultrastructure Research*, vol. 83, pp. 220–231, 1983.
Hydrogel Keratophakia in Non–Human Primates; Binder, P. S., Deg, J. K., and Zavala, E. Y., *Current Eye Res.*, 1:535, 1982.
Hydrogel Implants for the Correction of Myopia; Binder, P. S., *Current Eye Res.*, 2:7, 1982/1983.

List continued on next page.

*Primary Examiner*—Paul E. Konopka
*Attorney, Agent, or Firm*—Scott R. Miller

[57] ABSTRACT

A seton constructed of a hydrogel material is surgically implanted beneath a limbus-based scleral flap and extending into the anterior chamber of the eye in order to alleviate excessive intraocular pressure. Once implanted, the seton permits migration of aqueous to the area beneath the conjunctiva, thereby reducing the intraocular pressure. The material from which the seton is constructed as a material which is biocompatible with the tissue in the eye such as, for example, a hydrogel material having a water content ranging from approximately 30% to approximately 79%.

38 Claims, 1 Drawing Sheet

OTHER PUBLICATIONS

Hydrophilic Lenses for Refractive Keratoplasty; the use of Factory Lathed Materials, Binder, P. S., Baumgartner, S. D., Deg, J. K., Zavala, E. Y., *CLAO Journal,* 10:105, 1984.

Hydogel Refractive Keratoplasty; Lens Removal and Exchanges, Binder, P. S., Zavala, E. Y., Deg, J. K., *Cornea,* 2:119, 1984.

Morphology of Hydrogel Implants Used for Refractive Keratoplasty; Samples, J. R., Binder, P. S., Baumgartner, S. D., *Invest Ophthalmol Vis. Sci.* 25:843, 1984.

Alloplastic Corneal Implants for the Correction of Refractive Errors, Binder P. S., Zavala, E. Y., Baumgartner, S. D., Deg, J. K., *Ophthalmology,* 91:806, 1984.

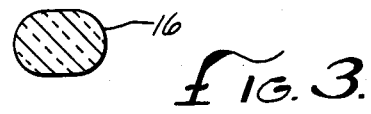
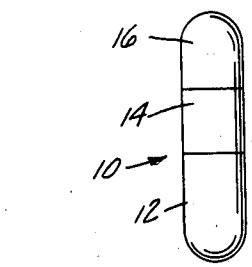
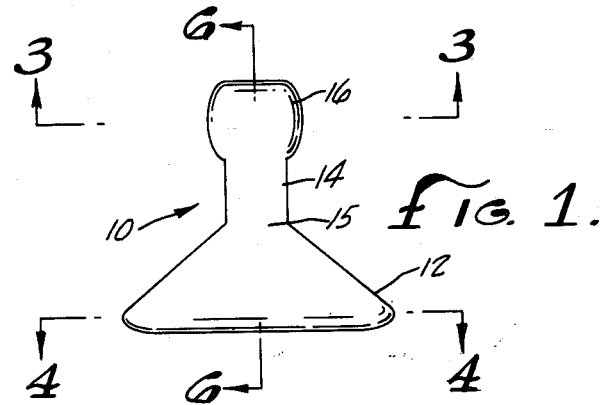
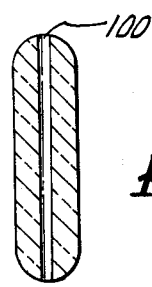
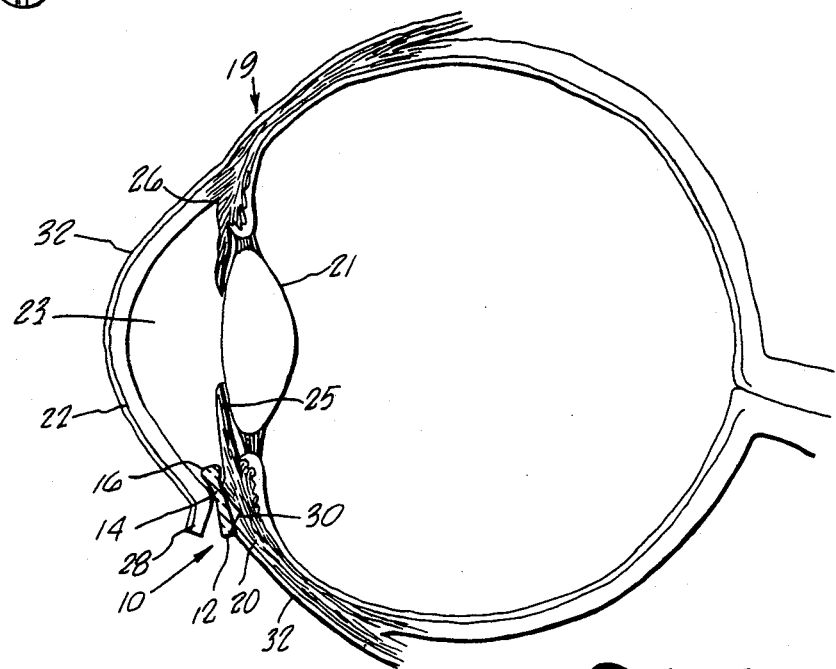

HYDROGEL SETON

This is a continuation of application Ser. No. 767,190, filed Aug. 19, 1985, now abandoned which is a continuation in part of application Ser. No. 597,530, filed Apr. 6, 1984 now U.S. Pat. No. 4,634,418.

BACKGROUND OF THE INVENTION

The field of the invention is treatment of eye disorders, and more particularly setons used to treat uncontrolled intraocular pressure.

Glaucoma is a disease of the eye which affects a substantial number of people. It involves uncontrolled intraocular pressure within the eye which is typically caused by obstruction of the trabecular meshwork. The disease is serious since it often results in permanent damage to the optic nerve. Surgical treatment of glaucoma has been limited due to failure to control intraocular pressure as well as post-operative complications which tend to exacerbate the pre-operative conditions.

The eye is a complex part of the body. In general terms, the outer surface of the eye is covered with a thin filmy layer known as the conjunctiva. The conjunctiva is adjacent to the cornea and, among other things, serves to produce tears which protects the cornea from exposure to the outside environment. The tissue surrounding the eye is known as sclera.

The cornea acts to refract light through the area behind the cornea, known as the anterior chamber, and towards the lens. The size of the entrance aperture of the eye, known as the pupil, is controlled by muscles within the eye. The iris is positioned behind the anterior chamber and acts to permit the eye to focus on objects which are close or far away.

The retina is positioned in the back of the eye; the remaining portion of the eye behind the lens and iris being known as the vitreous chamber. The lens acts to focus the light coming from the pupil, through the vitreous chamber and onto the retina where the images are processed by the brain.

The fluid within the eye, known as aqueous humor or aqueous, is produced by the ciliary body and normally migrates through the pupil and into the anterior chamber where it is communicated through the trabecular meshwork and into the aqueous veins, which form fluid collection channels beneath the conjunctiva. Glaucoma results when the intraocular pressure is not relieved by the above-described normal aqueous migration.

Medical treatment of the uncontrolled high pressure of glaucoma has had varying success. Medicines in the form of eye drops or pills act to reduce the production of aqueous in the ciliary body and/or increase the outflow of aqueous through the trabecular meshwork are often used. Doctors have also attempted to treat glaucoma through what are generally known as surgical filtration procedures. One such technique creates a hole through the limbus under the sclera and excises a piece of the trabecular meshwork (trabeculectomy). After such filtration surgery, the aqueous is supposed to flow from the anterior chamber through the excised surgical area and into the space beneath the conjunctiva and sclera where it is finally absorbed by the body.

Another surgical technique to attempt to improve the filtration through the trabecular meshwork involves placing several Argon laser burns throughout the entire circumference of the trabecular meshwork in hopes of opening up the trabecular meshwork spaces. This procedure is called Argon laser trabeculoplasty.

In certain high risk cases, the above-described surgical techniques are typically unsuccessful due to the post-operative scarring of the wound or the scleral tissue. This scarring prevents migration of the aqueous out of the eye and results in a recurrence of the uncontrolled intraocular pressure of glaucoma.

Another attempt to relieve the uncontrolled high pressure of glaucoma is to perform what is known as an iridencleisis. The procedure involves pulling a piece of the iris through the wound from the anterior chamber to lie under the sclera and conjunctiva. Serious infection and inflammation of the wound often results from this procedure.

An additional technique implants a piece of cartilage into the eye. This procedure typically fails due to the formation of scar tissue about the wound resulting in the total closure of the wound which prevents the migration of aqueous.

Finally, seton implants in the form of polypropylene tubing and a device known as a Krupin Valve implant have failed due to post-operative extrusion of the implants through the wound as well as the formation of blood and fibrin clots and scar tissue in the area of implantation which act to inhibit the flow of aqueous. In addition, where the seton material is not biocompatible with the eye, serious infection, biological rejection and the formation of scar tissue typically prevent such seton implants from being successful.

In cases where medicines, laser trabeculoplasty and surgical filtration procedures, such as a trabeculectomy, have failed, the only medically proven method for controlling pressure within the eye is to permanently damage the ciliary body, i.e. the part of the eye which produces the aqueous. This procedure, known as Cyclocryotherapy, involves externally freezing the sclera above the ciliary body. This process kills the ciliary body and, in addition, eradicates all functioning or potentially functioning trabecular meshwork in the area and is fraught with complications including bleeding within the eye and raises a significant risk of total loss of use of the eye.

SUMMARY OF THE INVENTION

In order to reduce excessive intraocular pressure it is necessary to allow aqueous to migrate out of the eye. The invention disclosed herein is a device which is biocompatible with the tissue in the eye and allows fluid to migrate to the space under the conjunctiva without allowing bacteria to ingress into the eye.

Preferably, the seton is made from a hydrogel or hydrophilic material which is biocompatible with the tissue of the eye. Typically, such hydrogel material has a water content ranging from approximately 30% to approximately 79%. The seton is implanted within the eye by creating a limbus-based conjunctival flap and inserting part of the seton into the anterior chamber under a scleral flap. The scleral flap is then sutured closed and covered with conjunctiva in such a way that aqueous is permitted to migrate to the area beneath the conjunctiva. The seton is shaped so as to retain its position once it is implanted within the eye and provide adequate surface area to accommodate the migration of the aqueous.

The shape of the seton acts to prevent extrusion of the device through the wound. In addition, the shape and the biocompatible properties of the hydrogel material act to inhibit the formation of scar tissue to an extent which would close-off the aqueous migration path. Aqueous is permitted to flow about the surface of the device and, in one embodiment of the present device, through a conduit through the center of the device. Moreover, due to the porosity of the hydrogel material of the device, it is possible that aqueous may also migrate through the device without the use of a conduit. Thus, this device allows intraocular pressure to be reduced in a controlled fashion while preventing bacteria from entering the eye.

An object of the invention is to provide a means and method for treating the excessive intraocular pressure with a material that is biocompatible with the ocular tissues.

An additional object of the invention is to provide a means to relieve excessive intraocular pressure in a controlled fashion and at the same time prevent bacteria from entering the eye.

A further object of the invention is to provide a device that reduces intraocular pressure while retaining its position once surgically implanted within the eye.

A further object of the invention is to provide a means for relieving excessive intraocular pressure which will not permanently damage the eye or its ability to function normally.

A further object of the invention is to provide a means for relieving the excessive intraocular pressure of glaucoma which will not be defeated by the normal subsequent scarring process of the ocular tissues. Other and more detailed objects and advantages of the invention will become apparent from examination of the description and drawings herein.

DETAILED DESCRIPTION OF THE DRAWINGS

FIG. 1 is a front view of an embodiment of the seton;

FIG. 2 is a side view of an embodiment of the seton;

FIG. 3 is a cross-sectional view of an embodiment of the seton taken substantially along line 3—3 of FIG. 1;

FIG. 4 is a cross-sectional view of an embodiment of the seton taken substantially along line 4—4 of FIG. 1;

FIG. 5 is a cross-sectional view showing an embodiment of the seton implanted in an eye; and, FIG. 6 is a cross-sectional view of a second embodiment of the seton.

DETAILED DESCRIPTION OF THE PREFERRED EMBODIMENTS OF THE INVENTION

As shown in FIGS. 1-4, the seton 10 has a base portion 12 which is essentially triangular in shape. A neck portion 14 extends from the upper corner 15 of the triangular base portion 12. A lip portion 16 is formed about the upper end of the neck portion 14 furthest from the triangular base portion 12. As can be seen clearly in FIGS. 2-4, the seton has a cross-section which varies from substantially an ellipse at the neck 14 and lip 16 portions to substantially an oval at the lower end of the base portion 12.

The seton 10 is implanted into the eye 19, as illustrated in FIG. 5. A trabeculectomy procedure is performed under a limbus-based conjunctival flap by dissecting a rectangular piece of sclera 20 approximately 5 mm×5 mm in partial thickness into the clear cornea. An incision is made into the anterior chamber 23 using razor blade fragments on both sides of the subscleral wound to permit a rectangular-sized piece of cornea 22, Schwalbe's line and a portion of the filtration meshwork 26 measuring approximately 2 mm in vertical height and approximately 3 to 4 mm in length to be removed from the eye. The bed of the wound is appropriately cauterized to prevent bleeding. An iridectomy is performed when the iris 25 prolapses into the wound.

A seton 10 as described herein, with previously factory lathed edges is inserted into the wound. Preferably, the seton is made from a hydrogel or hydrophilic material which is biocompatible with the tissue of the eye. Typically, such hydrogel material has a water content ranging from approximately 30% to approximately 79%. The seton is implanted within the eye by creating a limbus-based conjunctival flap and inserting part of the seton into the anterior chamber under a scleral flap. The scleral flap is then sutured closed and covered with conjunctiva in such a way that aqueous is permitted to migrate to the area beneath the conjunctiva. The seton is shaped so as to retain its position once it is implanted within the eye and provide adequate surface area to accommodate the migration of the aqueous.

The shape of the seton acts to prevent extrusion of the device through the wound. In addition, the shape and the biocompatible properties of the hydrogel material act to inhibit the formation of scar tissue to an extent which would close-off the aqueous migration path. Aqueous is permitted to flow about the surface of the device and, in one embodiment of applicant's device, through a conduit through the center of the device. Moreover, due to the porosity of the hydrogel material of the device, it is possible that aqueous may also migrate through the device without the use of a conduit. Thus, this device allows intraocular pressure to be reduced in a controlled fashion while preventing bacteria from entering the eye.

The lip portion 16 of the seton 10 which is implanted into the anterior chamber 23 is slightly larger than the above described incision in the anterior chamber 23. By compressing the lip portion 16 of the seton 10 prior to insertion into the anterior chamber 23, the subsequent expansion of the lip portion 16 will act to maintain the position of the seton 10. The lip portion 16 thereby acts to prevent extrusion of the seton 10 from its desired placement in the eye and the anterior chamber into the subscleral space 30. In addition, if the lip portion 16 is formed as shown in FIGS. 2 and 4 such that the lip does not extend laterally from the front or rear of the neck portion 14 (i.e. to the left or right as shown in FIG. 2), aqueous migration along the surface of the seton device is enhanced by preventing occulusion of the surgical area by the iris 25.

The scleral flap 28 is then closed over the seton 10 with 2 interrupted 10-0 monofilament nylon sutures at the apices of the wound. So implanted, only the corners of the lower end of the triangular base portion 12 of the seton 12 will protrude from beneath the sutured scleral flap 28. The conjunctiva 32 is then closed over the entire surgical area with a continuous 10-0 monofilament nylon suture.

For purposes of example, it is anticipated that the preferred embodiment of the seton 10, as shown in FIG. 1, will be approximately 6 mm to 8 mm in length (L) and approximately 7 mm to 9 mm in width (W) at the base of the triangular base portion 12. The neck portion 14 is expected to have a major axis ($A_N$) of approximately 2 mm while the lip portion is expected to have a major axis ($A_L$) of approximately 3 mm to 4 mm. Similarly, as shown in FIGS. 2-4, it is anticipated that the preferred embodiment of the invention will have a thickness (t) of approximately ½mm.

The second embodiment of the device, shown in FIG. 6, includes a longitudinal conduit 100 of approximately ½mm in diameter formed from the upper end 16 through the neck portion 14 and the lower base portion 12. The remaining features of the device are sufficiently similar to the first embodiment that they are not described again. This conduit permits additional aqueous to migrate out of the eye. Again, due to the biocompatible nature of the hydrogel material and the shape of the seton 10, scarring, clotting and the like in the area of the ends of conduit, which would result in blockage of occlusion of the conduit, is prevented.

It is possible to attach a polypropylene suture (not shown) to the seton 10 so that it may be post-operatively retracted from its subscleral position should the eye become excessively soft, a condition known as hypotony. In addition, the seton 10 may be colored using presently available dyes for hydrogel lenses to enable easy visualization of the seton while it is implanted in the eye.

When properly inserted, the seton 10 acts to allow aqueous within the eye to migrate from the anterior chamber 23 to the space beneath the scleral flap 28. Such migration is typically accomplished by flow about the surface of the seton but may also be accomplished in part by flow through the seton 10 due to the porosity of the hydrogel material.

The base portion 12 of the seton 10 is enlarged and shaped so as to provide sufficient surface area to facilitate aqueous migration and yet permit a portion of the seton to extend from the sutured scleral flap while still allowing the conjunctiva to be conveniently closed over the implanted seton 10. It is expected that the base portion 12 of the seton 10 may be formed in shapes other than the triangular shape shown herein so long as such shapes permit the scleral flap and the conjunctiva to be closed about the lower end 12 of the seton 10 as described herein.

Serious infection of the eye is prevented since the conjunctiva acts to protect the implanted seton 10 from the atmosphere by entirely enclosing and covering the surgical site.

While described hereinabove in detail, it is anticipated that the description contained herein is for purposes of example only and should not be construed to limit the scope of the appended claims.

I claim:

1. A seton for relieving intraocular pressure comprising a body portion, said body portion having a cross section which varies from being substantially eliptical to substantially oval, a neck portion extending from said body portion, and a lip portion formed about said neck portion, said seton being made from a biocompatible porous hydrogel material.

2. A seton as set forth in claim 1 wherein said lip portion is at the end of said neck portion furthest from said body portion.

3. A seton as set forth in claim 1 wherein said seton material is a hydrogel material having a water content ranging from approximately 30% to approximately 79%.

4. A seton as set forth in claim 1 wherein said seton has a peripheral edge which is substantially rounded.

5. A seton for relieving intraocular pressure comprising a body portion, said body portion having a neck portion extending therefrom, a lip portion formed about said neck portion, and a conduit arranged to permit additional aqueous migration extending through said body portion and said neck portion of said seton, said seton being constructed from a biocompatible porous hydrogel material.

6. A seton as set forth in claim 5 wherein said lip portion is formed at the end of said neck portion furthest from said body portion.

7. A seton as set forth in claim 5 wherein said seton material is a biocompatible porous hydrogel material having a water content ranging from approximately 30% to approximately 79%.

8. A seton for relieving intraocular pressure comprising a body portion which is substantially triangular in shape and having a cross-section which varies from substantially elliptical to substantially oval, a neck portion extending from one corner of said body portion and a lip portion formed about said neck portion, said seton being made from a biocompatible porous hydrogel material.

9. A seton as set forth in claim 8 wherein said lip portion is at the end of said neck portion furthest from said body portion.

10. A seton as set forth in claim 8 wherein said biocompatible material is a biocompatible porous hydrogel having a water content ranging from approximately 30% to approximately 79%.

11. A seton as set forth in claim 8 wherein said seton has peripheral edge which is substantially rounded.

12. A seton as set forth in claim 8 wherein said seton is colored to enable easy visualization of the seton while in the eye.

13. A method for reducing excessive intra-ocular pressure, the steps comprising creating a limbus-based conjunctival flap and scleral flap by making an incision near the junction between the cornea and the sclera, excising a portion of the cornea, Schhwalbe's line, and the trabecular meshwork by making incisions into the anterior chamber beneath said flap, inserting a first end of a seton beneath said flap, said seton being made from a biocompatible porous hydrogel material, said first end including a lip portion and a second end including a body portion, said lip portion extending about a narrowed portion which extends from said body portion, said lip portion and said body portion being arranged to inhibit extrusion and extraction of said seton from the eye after said seton is implanted, suturing said flap about said seton such that said seton extends radially from the anterior chamber to the space beneath said flap and said second end extends in part from beneath said sutured flap, and covering said flap with conjectiva.

14. The method as set forth in claim 13, wherein the cross section of a portion of said first end of said seton is larger than said incision so as to maintain the postoperative position of said seton and said second end of said seton is substantially frusto-conical in shape.

15. The method as set forth in claim 13 wherein said second end of said seton is substantially larger in size than said first end of said seton.

16. The method as set forth in claim 14 wherein said seton has a conduit arranged to permit additional aqueous migration formed therethrough.

17. The method as set forth by claim 14 wherein said seton is made from a biocompatible porous hydrogel material having a water content ranging from approximately 30% to approximately 79%.

18. The method as set forth by claim 14 wherein the cross-section of a portion of said first end which is inserted in said incision through the sclera is larger than said incision so as to maintain the position of said seton and said second end of said seton is substantially triangular in shape and having a cross-section which varies from substantially elliptical to substantially oval.

19. A seton for relieving intraocular pressure comprising,
a body portion and a lip portion, said body portion having a first end, said first end having a narrowed portion which is arranged for insertion into the anterior chamber of a human eye, said lip portion being formed on said narrowed portion of said first end of said body portion to inhibit the extrusion of said first end of said seton from the eye when said seton is implanted in the eye and said body portion being of a size larger than said narrowed portion to prevent said seton from being drawn into the eye after said seton is implanted into the eye, said body portion and said lip portion being made from a biocompatible material which inhibits the formation of scar tissue to an extent which would close off the aqueous migration path provided by said seton.

20. A seton for reducing excessive intraocular pressure caused by glaucoma, comprising, a body portion, said body portion being substantially triangular in shape and having a cross section which varies from substantially elliptical to substantially oval, a neck portion extending from said body portion and a lip portion formed about said neck portion at the end of said neck portion farthest from said body portion, said seton being constructed from a biocompatible material which inhibits the formation of scar tissue to an extent which would close off the aqueous migration path provided by said seton.

21. A seton for relieving intraocular pressure comprising a body portion, said body portion having a cross section which varies from being substantially elliptical to substantially oval, neck portion extending from said body portion, and a lip portion formed about said neck portion, said seton being made from a biocompatible material which inhibits the formation of scar tissue to an extent which would close off the aqueous migration path provided by said seton.

22. A seton as set forth in claim 21 wherein said lip portion is at the end of said neck portion furthest from said body portion.

23. A seton as set forth in claim 21 wherein said seton material is a hydrogel material having a water content ranging from approximately 30% to approximately 79%.

24. A seton as set forth in claim 21 wherein said seton has a peripheral edge which is substantially rounded.

25. A seton for relieving intraocular pressure comprising a body portion, said body portion having a neck portion extending therefrom, said body portion being of a size larger than said neck portion to prevent said seton from being drawn into the eye after said seton is implanted into the eye, a lip portion formed about said neck portion, and a conduit arranged to permit additional aqueous migration extending through said body portion and said neck portion of said seton, said seton being constructed from a biocompatible material which inhibits the formation of scar tissue to an extent which would close off the aqueous migration path provided by said seton.

26. A seton as set forth in claim 25 wherein said lip portion is formed at the end of said neck portion furthest from said body portion.

27. A seton as set forth in claim 25 wherein said seton material is a hydrogel material having a water content ranging from approximately 30% to approximately 79%.

28. A seton for relieving intraocular pressure comprising a body portion which is substantially triangular in shape and having a cross-section which varies from substantially elliptical to substantially oval, a neck portion extending from one corner of said body portion and a lip portion formed about said neck portion, said seton being made from a biocompatible material which inhibits the formation of scar tissue to an extent which would close off the aqueous migration path.

29. A seton as set forth in claim 28 wherein said lip portion is at the end of said neck portion furthest from said body portion.

30. A seton as set forth in claim 28 wherein said biocompatible material is a hydrogel having a water content ranging from approximately 30% to approximately 79%.

31. A seton as set forth in claim 28 wherein said seton has a peripheral edge which is substantially rounded.

32. A seton as set forth in claim 28 wherein said seton is colored to enable easy visualization of the seton while in the eye.

33. A method for reducing excessive intraocular pressure, the steps comprising,
creating a limbus-based conjunctival flap and scleral flap by making an incision near the junction between the cornea and the sclera,
excising a portion of the cornea, Schwalbe's line and the trabecular meshwork by making incisions into the anterior chamber beneath said flap,
inserting a first end of a seton beneath said flap, said seton being made from a biocompatible material which inhibits the formation of scar tissue to an extent which would close off the aqueous migration path provided by said seton, said first end including a lip portion and a second end including a body portion said lip portion extending about a narrowed portion which extends from said body portion, said lip portion and said body portion are arranged to inhibit extrusion and extraction of said seton from the eye after said seton is implanted and,
suturing said flap about said seton such that said seton extends radially from the anterior chamber to the space beneath said flap and said second end extends in part from beneath said sutured flap, and covering said flap with conjunctiva.

34. The method as set forth in claim 33, wherein the cross section of a portion of said first end of said seton is larger than said incision so as to maintain the postoperative position of said seton and said second end of said seton is substantially frusto-conical in shape.

35. The method as set forth in claim 33 wherein said second end of said seton is substantially larger in size than said first end of said seton.

36. The method as set forth in claim 34 wherein said seton has a conduit arranged to permit additional aqueous migration formed therethrough.

37. The method as set forth by claim 34 wherein said seton is made from a hyrogel material having a water content ranging from approximately 30% to approximately 79%.

38. The method as set forth by claim 34 wherein the cross-section of a portion of said first end which is inserted in said incision through the sclera is larger than said incision so as to maintain the position of said seton and said second end of said seton is substantially triangular in shape and having a cross-section which varies from substantially elliptical to substantially oval.

* * * * *